United States Patent
Wang et al.

(10) Patent No.: US 7,884,203 B2
(45) Date of Patent: Feb. 8, 2011

(54) METHOD OF SUCRALOSE SYNTHESIS YIELD

(75) Inventors: Fei Wang, Nanjing (CN); Haibing He, Nanjing (CN); Xin Yang, Nanjing (CN); Yongzhu Yu, Nanjing (CN); Zhisong Fan, Nanjing (CN)

(73) Assignee: JK Sucralose Inc., Sheyang County, Jiangsu (CN)

( * ) Notice: Subject to any disclaimer, the term of this patent is extended or adjusted under 35 U.S.C. 154(b) by 1111 days.

(21) Appl. No.: 11/427,081

(22) Filed: Jun. 28, 2006

(65) Prior Publication Data

US 2007/0207246 A1    Sep. 6, 2007

(30) Foreign Application Priority Data

Mar. 6, 2006    (CN) .................. 2006 1 0038635

(51) Int. Cl.
*C07H 5/02*    (2006.01)
(52) U.S. Cl. ...................................... 536/122
(58) Field of Classification Search ........................ None
See application file for complete search history.

(56) References Cited

U.S. PATENT DOCUMENTS

| | | | |
|---|---|---|---|
| 4,889,928 A | 12/1989 | Simpson | |
| 4,977,254 A | 12/1990 | Homer et al. | |
| 5,449,772 A | 9/1995 | Sankey | |
| 5,498,709 A | * | 3/1996 | Navia et al. .................. 536/124 |

FOREIGN PATENT DOCUMENTS

| | | |
|---|---|---|
| CN | 1453284 | 11/2003 |
| CN | 1526716 | 9/2004 |
| EP | 0043649 | 1/1982 |
| WO | WO2004104016 | * 2/2004 |

OTHER PUBLICATIONS

SigmaAldrich "Amberlyst 15"; also available at http://www.sigmaaldrich.com/catalog/ProductDetail.do?D7=0&N5=Product%20No.%7CBRAND_KEY&N4=216399%7CALDRICH&N25=0&QS=ON&F=SPEC; last viewed Sep. 8, 2009.*
Michigan State University, Specialized Acylation Reagents and Techniques; also available at http://web.archive.org/web/20020917022615/http://www.cem.msu.edu/~reusch/VirtualText/special2.htm; published Sep. 2002; last viewed Sep. 8, 2009.*
New World Encyclopedia "azo compound"; also available at http://www.newworldencyclopedia.org/entry/Azo_compound; last viewed Sep. 9, 2009.*
Burke, John, Solubility Parameters: Theory and Application, Part 2—The Hildebrand Solubility Parameter; also available at http://cool.conservation-us.org/byauth//burke/solpar/solpar2.html; published Aug. 1984; last viewed Sep. 11, 2009.*
UCLA, Special Topics: Recrystallization; also available at http://www.chem.ucla.edu/~bacher/Specialtopics/Recrystallization.html; published Jun. 2003; last viewed Sep. 11, 2009.*
Montalbetti, Christian A.G.N. and Falque, Virginie, Tetrahedron, vol. 61, pp. 10827-10852 (2005).*
March, Jerry and Smith, Michael B., March's Advanced Organic Chemistry: Reactions, Mechanisms, and Structure, Fifth Edition, copyright 2001, Chapter 10, pp. 484-486.*

* cited by examiner

*Primary Examiner*—Shaojia Anna Jiang
*Assistant Examiner*—Bahar Schmidtmann
(74) *Attorney, Agent, or Firm*—Global IP Services; Tianhua Gu

(57) ABSTRACT

The invention discloses a method for improving the yield of sucralose, including reacting sucrose to produce sucrose-6-acetate in the existence of an azo reagent as a catalyst and acetic acid as an acylating agent in a proper solvent; then reacting sucrose-6-acetate with a proper chlorinating agent to produce sucralose-6-acetate in a non-proton polar solvent with TCA as a catalyst; and at last, alcoholyzing sucralose-6-acetate in KOH/methanol to obtain sucralose.

5 Claims, No Drawings

METHOD OF SUCRALOSE SYNTHESIS YIELD

CROSS REFERENCE TO THE RELATED PATENT APPLICATION

This patent application claims the priority right of the Chinese patent application No. 200610038635.6, filed on Mar. 6, 2006.

TECHNICAL FIELD OF THE INVENTION

The invention falls in the field of chemical synthesis. It refers to the synthesis of sucralose with an increasing yield.

BACKGROUND OF THE INVENTION

As a new type of sweetener, sucralose is a kind of chlorinated sucrose. It is 600 times sweeter than sucrose, and does not participate in the human metabolism. Sucralose has shown high safety and strong ability of anti-acidolysis. All of these advantages make sucralose to become a most popular and strong sweetener in the market. Up to the present, it has been approved for use in more than thirty countries. Studies on the synthesis of sucralose began from 1970s. Current syntheses of sucralose mainly include methods of mono-group protection and omni-group protection, of which the latter has not been commonly used because of its low yield and complicated operation. Many studies refer to the method of mono-group protection, such as U.S. Pat. No. 4,889,928, U.S. Pat. No. 5,449,772, CN1453284 and CN1526716, which have focused on the synthesis of sucrose-6-acetate with only a little study on the follow-up chlorination and alcoholysis.

U.S. Pat. No. 4,977,254 has disclosed a reaction of chloro-sulfoxide with a catalytic amount of benzyl tri-ethyl ammonium chloride in DCE, and the yield of this reaction is only 21%. European patent No. EP0043649 has disclosed a reaction of chloro-sulfoxide with pyridine in chloroform at 75° C. Since the reaction condition is too critical, it is difficult to reach in the production. Moreover, pyridine is toxic and in a bad odor. Most of the present chlorination processes need to be conducted in a high temperature, and has a serious charring phenomenon and a low yield. In the prior art, sodium methoxide was used in the alcoholysis of sucralose ester, e.g., in CN1453284 A, and there exists a problem of incomplete reaction.

In this invention, chlorination can be conducted under mild conditions with a conversation rate of over 80%. The general yield is about 50% after the crystallization. In most studies (such as CN1453284 A), sodium methylatesodium methoxide has been used as a catalyst in the alcoholysis of sucralose easter, but the disadvantage is that it can not be reacted completely. In this invention, we use KOH as a catalyst in the alcoholization in methanol solution at a proper temperature, to enable a complete reaction without creating any foreign materials.

SUMMARY OF THE INVENTION

Aimed at the above technical problems, the purpose of this invention is to provide a method for improving the yield of sucralose, which is in a low cost, a high yield and a good quality of product, and the process is simple, the reaction conditions are mild and the production is stable.

The invention is realized with the support of the following technical measures:

The invention provides a method for improving the yield of sucralose, characterized in: reacting sucrose to produce sucrose-6-acetate in the existence of an azo reagent as a catalyst and acetic acid as an acylating agent in a proper solvent; after being crystallized from a mixed solution of DMF & acetone, the purified sucrose-6-acetate being reacted with a proper chlorinating agent to produce sucralose-6-acetate in a non-proton polar solvent with TCA as a catalyst; then the crude sucralose-6-acetate being recrystallized from a mixed solution of water and alcohol; and at last, the purified sucralose-6-acetate being alcoholyzed in KOH/methanol to obtain sucralose.

In the method of the invention, the azo reagent used is selected from diethyl azodicarboxylate and N,N-dicyclohexylcarbodiimide (DCC).

In the method of the invention, acetic acid used in the synthesis of sucrose-6-acetate is 1.4-1.5 times the amount of sucrose in mole, and the catalyst is 0.1-0.3 times the amount of sucrose in mole.

In the method of the invention, the solvent used in the synthesis of sucrose-6-acetate is selected from N,N-dimethylformamide (DMF) and hexamethyl phosphoramide.

In the method of the invention, the reaction temperature is from 10° C. to 25° C. in the step of synthesis of sucrose-6-acetate In the method of in invention, the temperature in the step of crystallization of sucrose-6-acetate from the mixed solution of DMF and acetone is in a range from 30° C. to 50° C. And the ratio of acetone to DMF is 2:1~5:1 in volume.

In the method of the invention, the proper chlorinating agent is selected from phosphorous pentachloride, Phosphorus trichloride, phosphorus oxychloride, chloro-sulfoxide and phosgene.

In the method of the invention, the non-proton polar solvent is selected from N,N-dimethylformamide (DMF), hexamethyl phosphoramide and dimethyl sulfoxide.

In the method of the invention, the chlorinating agent used in the step of chlorination of sucrose-6-acetate into sucralose-6-acetate is 4-7 times amount of sucrose-6-acetate in mole, and TCA is 3-5 times amount of sucrose-6-acetate in mole.

In the method of the invention, the temperature of chlorination from sucrose-6-acetate into sucralose-6-acetate is in a range from −5° C. to 80° C.

In the method of the invention, the alcohol used in the mixed solution of alcohol and water in the step of crystallization of sucralose-6-acetate is selected from methanol, ethanol, propanol and isopropyl alcohol.

In the method of the invention, the concentration of alcohol used in the mixed solution of alcohol and water in the step of crystallization of sucralose-6-acetate is in a range from 10% to 50%.

In the method of the invention, the temperature in the crystallization of sucralose-6-acetate from the mixed solution of acetone/DMF is in a range from 55° C. to 75° C.

In the method of the invention, the pH value in the system of alcoholysis of sucralose-6-acetate is in a range from 10 to 11.

In the method of the invention, the temperature of alcoholysis of sucralose-6-acetate is in a range from 45° C. to 50° C.

The schemes of the synthesis of sucralose from sucrose in a high purity are as follows:

1. Synthesis of Sucrose-6-Acetate

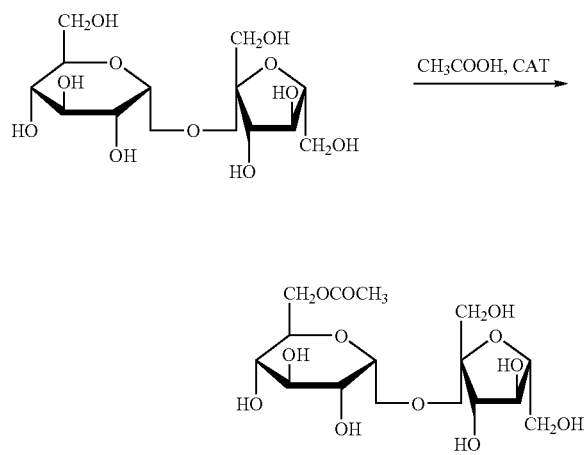

In the existence of diethyl azodicarboxylate, sucrose is reacted with acetic acid, highly selectively, to produce sucrose-6-acetate with very little esterification in other positions. The reaction conditions are mild and the reaction can be done in a room temperature. Usually, the reaction is completed in 2-8 hours. The conversion rate of sucrose is over 95%. Under the same conditions, using N,N-dicyclohexyl-carbodiimide (DCC) instead of diethyl azodicarboxylate, the conversion rate of sucrose is still around 90%. Acetic acid used is about 1.5 times the amount of sucrose in mole. The content of impurities will be increased obviously with the increasing amount of acetic acid.

2. Synthesis of Sucralose-6-Acetate

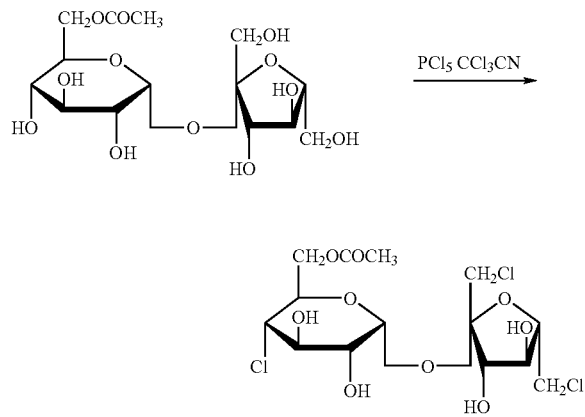

In the synthesis of sucralose-6-acetate, we were surprised to find that the reaction temperature could be greatly reduced in the existence of trichloro acetonitrile (TCA) and the reaction could be completed in a temperature around 80° C. In DMF, chlorinating agents, such as phosphorous pentachloride, exist in an ion form; their sublimation temperature is 160° C. and the reaction can be conducted successfully below 80° C. Chlorination process can be easily controlled. It can be completed in 8-12 hours without charbonization phenomenon. The product can be crystallized from water in a high purity.

3. Synthesis of Sucralose

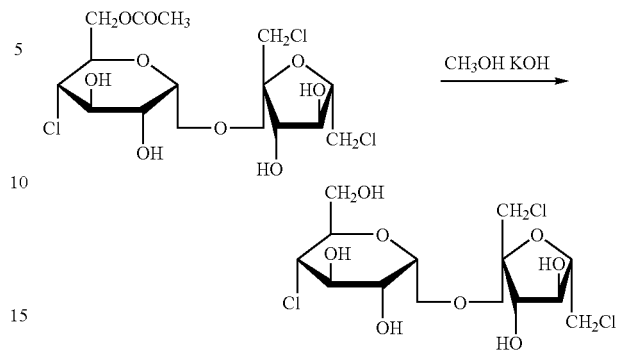

The deacetylation of sucralose-6-acetate is conducted in a high yield in a methanol solution with KOH as catalyst. The conversation rate is over 90%. In this process, the control of the pH value is crucial. If the pH value is higher than 11, impurities will be increased. If it is lower than 10, the conversation rate will be very low. The pH value is adjucteded by controlling the amount of KOH. Reaction temperature is controlled in a range of 45° C. to 50° C.

Adopting the above synthesis process, the yield can be more than 35% of sucrose in weight.

The benefits of this invention:

In comparison with the previously reported sucralose production processes, the invention has characteristics such as a low cost, a high yield, a good quality, a simple process, mild reaction conditions, and stable and easy production. It has passed a verification in a plant with an annual output of 15 MT, and has got perfect achievements. The quality of product complied with FCC and USP standards, and the weight yield rate is stablely more than 35%.

DETAIL DESCRIPTION OF THE INVENTION

Although the following detailed description contains many specifics for the purposed of illustration, any one of ordinary skill in the art will appreciate that many variations and alterations to the following details are within the scope of the invention. Accordingly, the following preferred embodiments of the invention are set forth without any loss of generality to, and without imposing limitations upon, the claimed invention.

Example 1

Synthesis of Sucrose-6-Acetate 34.2 g sucrose was suspended in 200 ml DMF, and 3.5 g of diethyl azodicarboxylate was added into the mixture. After stirring for 30 minutes in room temperature, 8.8 g of acetic acid was dropped into the mixture. Then, the reaction mixture was stirred for 5 hours in room temperature, and added with 30 ml water and stirred for 30 min. The solvent was evaporated under a reduced pressure, and a floccule (35 g) was obtained. 30 ml of DMF was added into the floccule at around 40° C. Then 100 ml of acetone was dropped into the mixture with stirring. The resulting crystals were cooled, filtered and dried to obtain sucrose-6-acetate.

Example 2

Synthesis of Sucrose-6-Acetate 34.2 g of sucrose was suspended in 200 ml DMF, and 5 g N,N-dicyclohexylcarbodiimide (DCC) was added, After stirring for minutes in room temperature, 8.8 g of acetic acid was dropped into the mixture. Then, the reaction mixture was stirred for 4 hours in room temperature, and added with 10 ml water and stirred for 20 min. The solvent was evaporated under a reduced pressure to obtain a floccule, 35 g. 30 ml of DMF was added into the floccule at around 40° C. Then 100 ml of acetone was dropped into the mixture with stirring. The resulting crystals were cooled, filtered and dried to obtain sucrose-6-acetate.

Example 3

Synthesis of Sucralose-6-Acetate 35 g of sucrose-6-acetate and 110 g of $PCl_3$ were dissolved in 300 ml N,N-dimethylformamide (DMF), and the solution was cooled to −5° C. Then, 70 g of TCA was added. The temperature raised to 80° C. within 6 hours, and the reaction was conducted at this temperature for 3 hours. After cooling down, the solution was neutralized with a solution of $NaHCO_3$ in water. The neutralized solution was extracted with DCM, and the extract was decolored with activated carbon, then filtered. The filtrate was concentrated. To the concentrate, 250 ml water was added to obtain a solution in 75° C. This solution was cooled and crystals appeared, thus obtaining a crude product, sucralose-6-acetate, 26.2 g.

Example 4

Synthesis of Sucralose-6-Acetate 35 g of sucrose-6-acetate and 125 g of $PCl_3$ were dissolved in 300 ml N,N-dimethylformamide (DMF), and the solution was cooled to −5° C. Then, 90 g of TCA was added. The temperature raised to 80° C. within 6 hours, and the reaction was conducted at this temperature for 3 hours. After cooling down, the solution was neutralized with a solution of $NaHCO_3$ in water. The neutralized solution was extracted with DCM, and the extract was decolored with activated carbon, then filtered. The filtrate was concentrated. To the concentrate, 250 ml water was added to obtain a solution in 75° C. This solution was cooled and crystals appeared, thus obtaining a crude product, sucralose-6-acetate, 25 g.

Example 5

Purification of Sucralose-6-Acetate 20 g crude product of Sucralose-6-acetate was suspended in 30 ml of 10% solution of methanol in water. The mixture was heated to 70° C. to obtain a solution. It was cooled slowly to room temperature and crystals appeared. The mixture was filtered and crystals were dried to obtain pure product of Sucralose-6-acetate.

Example 6

Synthesis of Sucralose 20 g Sucralose-6-acetate was dissolved in 150 ml methanol, and the pH value of the solution was adjusted into 11 with KOH. The reaction was kept at 45° C. for 4 hours, then decolored with activated carbon, filtered and the filtrate was concentrated. 6 ml Water was added to the concentrate in 70° C. The resulting solution was Cooled gradually to room temperature and kept standing, then Filtered to obtain the product sucralose, 12.3 g. It was verified that the purity was over 99%.

What is claimed is:

1. An improved method for the synthesis of sucralose with an increasing yield comprising:
   reacting sucrose to produce sucrose-6-acetate in existence of an azo reagent as a catalyst and acetic acid as an acylating agent in a proper solvent at a temperature from 10° C. to 25° C., said azo reagent is selected from diethyl azodicarboxylate and N,N-dicyclohexylcarbodiimide (DCC);
   crystallizing sucrose-6-acetate from a mixed solution of DMF and acetone at a temperature from 30° C. to 50° C.;
   reacting the sucrose-6-acetate with a proper chlorinated reagent in the existence of trichloroacetonitrile as a catalyst, in a non-proton polar solvent at a temperature from 5° C. to 80° C. to obtain sucralose-6-acetate;
   crystallizing and purifying the sucralose-6-acetate from a mixed solution of alcohol and water at a temperature from 55° C. to 75° C.;
   alcoholyzing sucralose-6-acetate in KOH/methanol at a pH of 10-11 and a temperature from 45° C. to 50° C., thus a product of sucralose being synthesized;
   said acetic acid used in the synthesis of sucrose-6-acetate is from 1.4 to 1.5 times the amount of sucrose in mole, said catalyst of azo reagent is from 0.1 to 0.3 time the amount of sucrose in mole, and said solvent used in the synthesis of sucrose-6-acetate is selected from N,N-dimethylformamide (DMF) and hexamethyl phosphoramide; and
   a ratio of acetone and DMF used in the mixed solution in the step of crystallization and purification of sucrose-6-acetate is 2:1~5:1.

2. The improvement method of claim 1, wherein said non-proton polar solvent is selected from N,N-dimethylformamide (DMF), hexamethyl phosphoramide and dimethyl sulfoxide.

3. The improvement method of claim 1, wherein said proper chlorinating agent is selected from phosphorous pentachloride, phosphorus trichloride, phosphorus oxychloride, chloro-sulfoxide and phosgene, said chlorinating agent used is 4-7 times amount of sucrose-6-acetate in mole, and said trichloroacetonitrile used is 3-5 times amount of sucrose-6-acetate in mole.

4. The improvement method of claim 1, wherein said alcohol used in the mixed solution of alcohol and water in the step of crystallization and purification of the sucralose-6-acetate is selected from methanol, ethanol, propanol and isopropyl alcohol.

5. The improvement method of claim 1, wherein said concentration of the alcohol used in the mixed solution of alcohol and water in the step of crystallization and purification of the sucralose-6-acetate is in a range from 10% to 50%.

* * * * *